United States Patent
Feldman et al.

(10) Patent No.: US 6,868,371 B1
(45) Date of Patent: Mar. 15, 2005

(54) SYSTEM AND METHOD TO QUANTIFY APPEARANCE DEFECTS IN MOLDED PLASTIC PARTS

(75) Inventors: Sandra Freedman Feldman, Niskayuna, NY (US); Andrew Joseph Poslinski, Schenectady, NY (US); Harsha Mysore Hatti, Schenectady, NY (US); Craig Alan Cantello, Schenectady, NY (US); James Louis Cifarelli, Schenectady, NY (US); Kena Kimi Yokoyama, Latham, NY (US); Grigoriy Aleksandrovich Shmigol, Cohoes, NY (US); Hua Wang, Niskayuna, NY (US); James Paul Barren, Scotia, NY (US); Arthur Joseph Osborn, Catskill, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/303,409

(22) Filed: May 3, 1999

(51) Int. Cl.[7] ............................................. G06F 17/10
(52) U.S. Cl. ................. 703/2; 703/8; 703/6; 264/40; 264/75; 264/161; 356/406; 356/450; 356/456
(58) Field of Search .................. 703/9, 4, 5; 356/237.2, 356/456; 264/40, 161; 265/75

(56) References Cited

U.S. PATENT DOCUMENTS

| | | | | |
|---|---|---|---|---|
| 4,314,156 A | * | 2/1982 | Kuppermann et al. | 250/281 |
| 4,498,860 A | * | 2/1985 | Gahan | 425/562 |
| 4,920,385 A | * | 4/1990 | Clarke et al. | 356/237.2 |

(List continued on next page.)

FOREIGN PATENT DOCUMENTS

| | | | | |
|---|---|---|---|---|
| DE | 4231200 | | 9/1992 | |
| EP | 0757245 | | 5/1997 | |
| GB | 2288461 | | 10/1995 | |
| GB | 2 288 461 A | * | 10/1995 | .......... G01N/33/44 |
| JP | 04244487 | | 9/1992 | |
| WO | 9605040 | | 7/1995 | |
| WO | 9634730 | | 4/1996 | |

OTHER PUBLICATIONS

"Thermal desorption behavior of absorbed material on wafer surfaces" T. Jimbo, IEEE 0–7803–3752–2/97, 1997.*
"The Scientist and Engineer's Guide to Digital Signal Processing", S. W. Smith, California Technical Publishing, ISBN: 0–9660176–7–6, 1997.*
"Thermal desorption behavior of absorbed material on wafer surfaces" T. Jimbo, IEEE 0–7803–3752–2/97, 1997.*
"The Scientist and Engineer's Guide to Digital Signal Processing", S. W. Smith, California Technical Publishing, ISBN: 0–9660176–7–6, 1997.*
Feldman et al., "Blend Segregation Detection", U.S. Appl. No. 09/075,913; filed May 11, 1998.
Feldman et al., "Pattern Analyzer", U.S. Appl. No. 09/188,094; filed Nov. 9, 1998.
Feldman et al., "Coined Line Analyzer", U.S. Appl. No. 09/188,095; filed Nov. 9, 1998.

*Primary Examiner*—Jean R. Homere
*Assistant Examiner*—Fred Ferris
(74) *Attorney, Agent, or Firm*—Cantor Colburn LLP

(57) ABSTRACT

A spatially-resolved spectrometer is used to measure streaking in molded sample plastic parts produced using a molding tool with various mold inserts which produce certain desired topological surface features upon these sample plastic parts. The measurements from one or more of these sample plastic parts are then provided to a computerized device which appropriately filters the data and calculates overall data shape, average peak and valley shift, and a quality number indicative of data slopes. These calculations are then used to determine an optimum set of ingredients and processing conditions to be used for the full-scale plastic part production.

18 Claims, 13 Drawing Sheets

U.S. PATENT DOCUMENTS

| | | | | |
|---|---|---|---|---|
| 5,053,173 A | * | 10/1991 | Sticht | 264/39 |
| 5,149,547 A | * | 9/1992 | Gill | 425/145 |
| 5,208,648 A | * | 5/1993 | Batchelder et al. | 356/237.1 |
| 5,220,403 A | * | 6/1993 | Batchelder et al. | 356/450 |
| 5,254,304 A | * | 10/1993 | Adachi et al. | 264/328.1 |
| 5,387,381 A | * | 2/1995 | Saloom | 264/75 |
| 5,413,814 A | * | 5/1995 | Bowen et al. | 427/262 |
| 5,528,368 A | * | 6/1996 | Lewis et al. | 356/456 |
| 5,541,413 A | * | 7/1996 | Pearson et al. | 250/339.11 |
| 5,606,413 A | * | 2/1997 | Bellus et al. | 356/326 |
| 5,793,483 A | * | 8/1998 | Zehnpfennig et al. | 356/139.03 |
| 5,804,117 A | * | 9/1998 | Baba et al. | 264/161 |
| 5,859,708 A | * | 1/1999 | Feldman | 356/406 |
| 5,943,127 A | * | 8/1999 | Feldman et al. | 356/237.2 |
| 6,002,480 A | * | 12/1999 | Izatt et al. | 356/479 |
| 6,045,502 A | * | 4/2000 | Eppstein et al. | 600/306 |
| 6,075,608 A | * | 6/2000 | Feldman et al. | 356/406 |
| 6,078,398 A | * | 6/2000 | Feldman et al. | 356/402 |
| 6,155,331 A | * | 12/2000 | Langer et al. | 164/456 |
| 6,214,560 B1 | * | 4/2001 | Yguerabide et al. | 435/7.1 |
| 6,258,301 B1 | * | 7/2001 | Feuerherm et al. | 264/40.1 |
| 6,259,093 B1 | * | 7/2001 | Wakiyama et al. | 250/306 |
| 6,441,901 B2 | * | 8/2002 | McFarland et al. | 356/364 |
| 6,485,413 B1 | * | 11/2002 | Boppart et al. | 600/160 |

* cited by examiner

FIG. 7 Description of signal peaks
L vs x positon for compressed and first iteration of peak and valley detection data FIG. 8  Description of signal peaks
L vs x position for first and second iteration of peak and valley detection

FIG. 9 Description of signal peaks
L vs x position for second iteration and third iteration of peak and valley detection Description of signal peaks

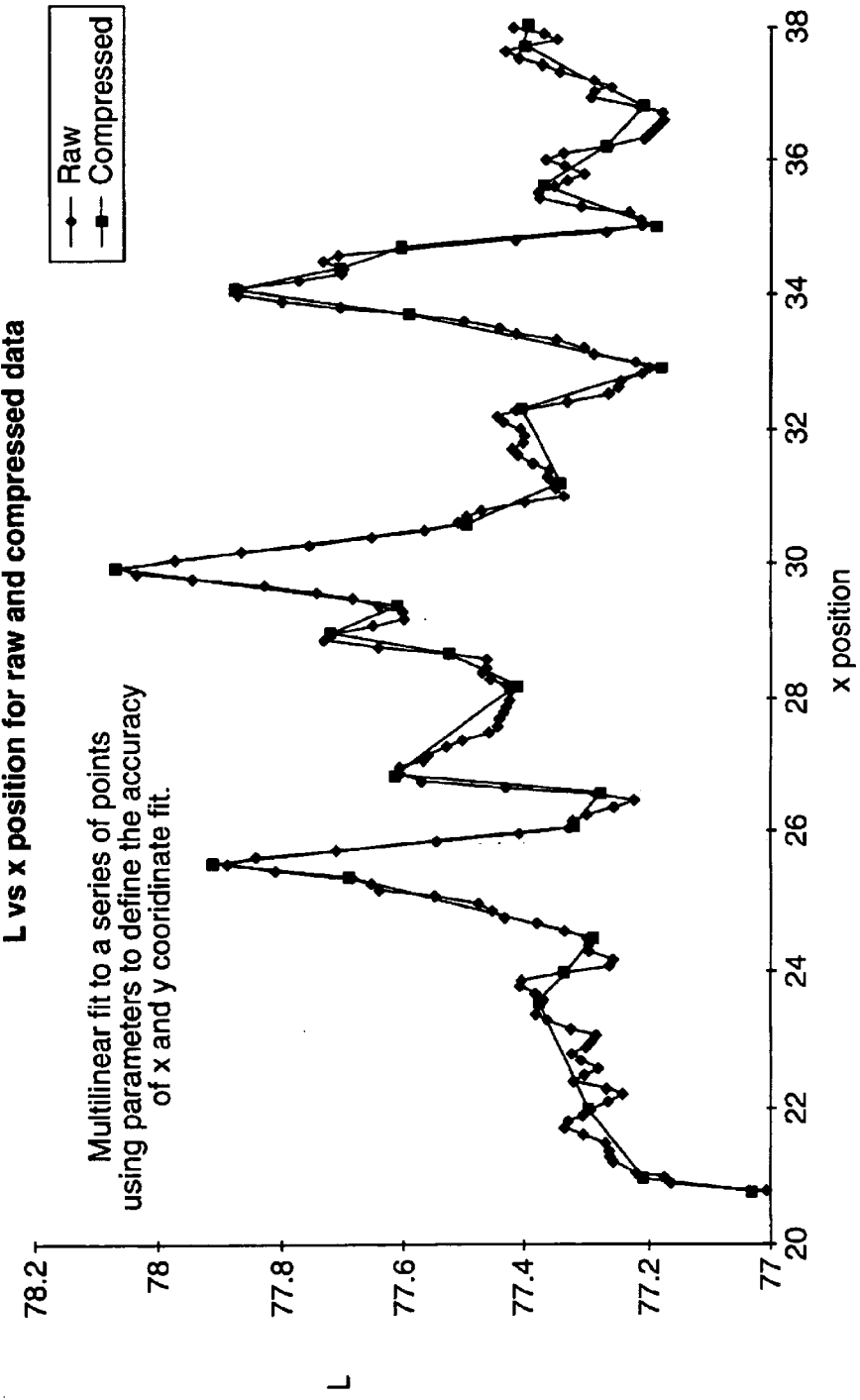
FIG. 12  L Shift Calculation ( similar for a shift and b shift clcultions)

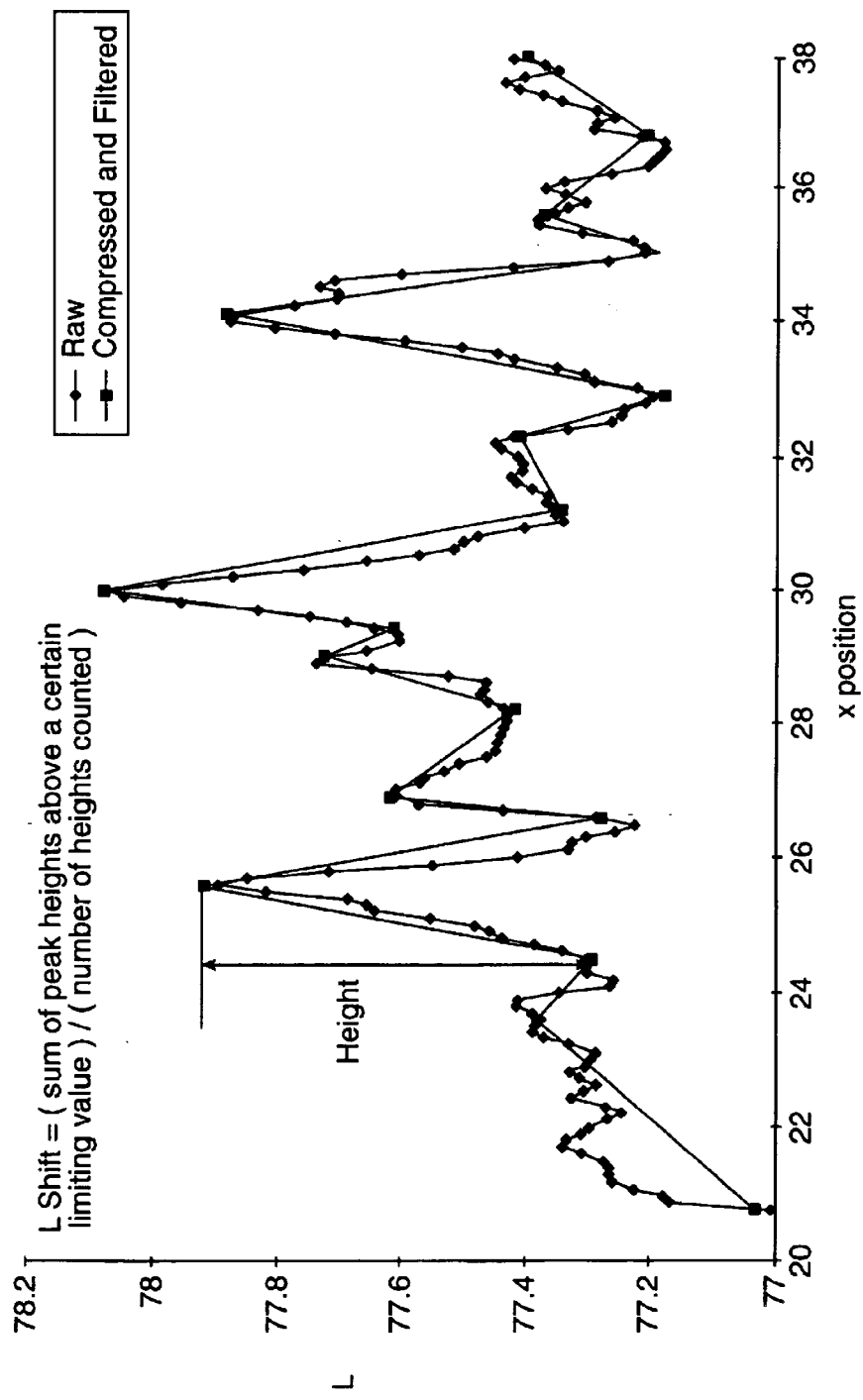
FIG. 13 L Shift Calculation (similar for a shift and b shift calculations)

SYSTEM AND METHOD TO QUANTIFY APPEARANCE DEFECTS IN MOLDED PLASTIC PARTS

BACKGROUND OF THE INVENTION

This invention relates generally to measuring appearance variations in molded plastic parts, and specifically to tools for duplicating the streaking seen in real parts and measurement and analysis of the streaking.

Consumers of durable plastic products including, for example, toys, computer and printer housings, and vehicles expect a uniform surface finish with no visible flaws, streaks, or defects. Common defects include streaks where various plastic flows meet in a part. These streaks may arise as different flow fronts from different gates meet or downstream of flow disruptions such as grills, bosses, ribs, or holes.

Currently, few, if any, numerical specifications related to uniformity of appearance are given to a supplier of raw plastic products outside of average color and possibly gloss or haze. Nevertheless, the molder creating the part and the consumer each expect a product with no visible flaws. The consumer, in particular, may view appearance defects as both unsightly and as indicative of poor quality material.

Currently, the quality, uniformity, and lack of defects in a part is typically judged using visual inspection on production parts. This leads to an absence of numerical specifications, lack of consistency due to operator variation, and an inability to consistently and rapidly process a large number of samples. Further, a large amount of waste may be generated since a large number of defective parts must be molded to attempt to quantify the problem. Often, the molder or customer is unable to transmit a complaint to the plastic supplier that is more specific than "a streaking problem exists," and many pounds of rejected production parts are shipped back to the plastic supplier for subsequent visual evaluation. Yet, it is difficult for the supplier to address the problem and provide solutions in the absence of effective measurement tools.

Several prior commonly-assigned and invented patents and patent applications, namely, U.S. Pat. No. 5,859,708, issued Jan. 12, 1999; and application Ser. Nos. 09/075,913; 09/188,094; and 09/188,095; address vagaries of visual inspection via a spatially resolved spectrometer which can resolve small defects that are not apparent to a standard spectrometer with the typical ½ inch diameter or larger aperture. Further, unlike the few spectrometers capable of smaller apertures that are not automated, the spectrometer described earlier may be interfaced with a computer for motorized sample movement and automatic data collection.

However, several problems remain. First, complex, curved, or textured parts are not amenable to automated inspection. Second, this spatially resolved spectrometer generates massive amount of data and automated data reduction is necessary to screen parts.

Accordingly, there is a need in the art for and improved system and method to quantify appearance defects in molded plastic parts,

SUMMARY OF THE INVENTION

A molding tool that duplicates streaking seen in real parts is used to produce molded plastic part samples that include selected topological surface features (e.g., ribs, holes, grills, bosses) of production molded parts to be subsequently produced. A spatially-resolved spectrometer is used to measure color characteristics spatially along the sample part. Finally, a computerized device is used to appropriately filter the data and quantify the streaking in terms of overall data shape, average peak and valley shift, and a quality number indicative of data slopes. Based on this process, which process may be iteratively applied to one or more series of samples, an optimal prescription of ingredients (e.g. plastic pellet characteristic, color dye mixes) and production conditions (e.g., temperature, extrusion rate) is identified for producing the production molded parts.

Once these optimal ingredients and conditions are specified, the production molded parts can then be produced properly the first time, in a way that minimizes streaking given the particular surface topology of those parts. This saves the time and expense of unsuccessful, defective production runs.

BRIEF DESCRIPTION OF THE DRAWING

FIGS. 12 and 13 illustrate the method used to average the degree of variation from peak to valley over the entire sample, using the sample raw data of FIG. 6.

DETAILED DESCRIPTION OF THE INVENTION

The several commonly-invented and commonly-assigned issued and pending U.S. patents noted earlier disclose a spatially-resolved spectroscopic tool for measuring visual characteristics of plastics, such as color, color blending, coining (e.g. scratching), etc.

The system and method, according to one embodiment of the invention, generally comprises three parts: A molding tool that duplicates the streaking seen in real parts, the a spatially resolved spectrometer to measure color along the surface of the part, and post processing software to quantify the streaking. Various parts of the system may also be used alone, as appropriate.

As used herein, the term "samples" will be used to refer to molded plastic parts produced by a molding tool according to the invention, while "production" will be used to refer to a molded plastic part (such as a computer monitor housing, a printer housing, a television housing) that is the ultimate object to be produced using the analysis tools provided according to the invention. In this context, the invention involves creating and using "sample" plastic parts to determine the optimum prescription for producing "production" plastic parts, so that defective production of production parts, and the cost and time for producing such production parts, is minimized.

Figure 1:
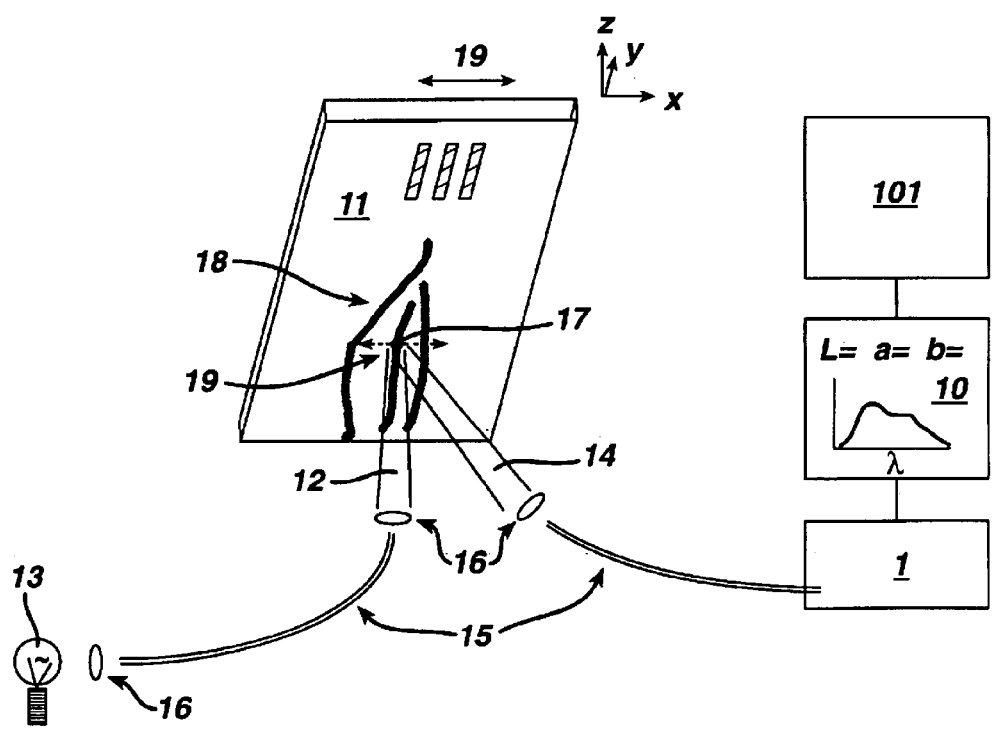
FIG. 1 is a schematic illustration of a spatially-resolved spectrometer according to one embodiment of the invention, for obtaining color readings from a plastic part being examined and analyzed.

As illustrated in FIG. 1, spatially-resolved spectrometer 1 is used in a manner similar to the disclosure of the above-referenced pending and issued U.S. patents. Color measured by spectrometer 1 is output in any conventional color format 10, such as but not limited to, CIELab units L, a, b. A molded plastic part 11 (which plastic part 11 may be a sample or a production part, but in this illustration is a sample) is evaluated by directing incident light 12 from a light source 13 onto plastic part 11 at a sample point 17, and reflected light 14 from sample point 17 is measured using spectrometer 1. Incident light 12 and reflected light 14 are carried to and from plastic part 11, for example, via light carriers 15 such as optical fibers, and are focused at sample point 17 as needed using focusing elements 16 such as one or more optical lenses. Incident light 12 may or may not be "focused" at sample point 17 in the scientific sense; so sample point 17 is simply to be understood as a point upon which light impinges 12 and is reflected 14. In order to evaluate streaking 18, plastic part 11 and sample point 17 are movable relative to one another in any direction along any combination of the x-y-z axes illustrated. A plurality of readings may thus be taken from different locations upon plastic part 11 at a plurality of locations spatially separated from one another by predetermined distances and directions. In this illustration, the samples are taken linearly 19 along the x axis. These readings are then input to the post-processing software for quantification and analysis. Molded plastic part 11, when it is a sample plastic part produced according to the invention, will also sometimes be referred to as a "mold" or "plaque." The color format measurements 10 are then forwarded to a computerized device 101 for post processing as described in FIGS. 4 through 13.

In one embodiment, spectrometer 1 and light carrier (e.g. fiber) couplings 15 are used in a 0–45 configuration, wherein incident light 12 impinges plastic part 11 at an angle of substantially zero degrees from perpendicular (i.e., normal to the plastic part 11 surface) and reflected light 14 is captured at an angle of substantially forty-five degrees from perpendicular. In other embodiments, incident light 12 angle is between zero and thirty, zero and forty five, and zero and eight-nine degrees from perpendicular. In other embodiments, reflected light 14 angle is between thirty and sixty, and between zero and eighty-nine degrees from perpendicular.

When a sample plastic part 11 is used, plastic part 11 may be mounted on a sample holder that is optionally mounted on motorized translation stages, so as to scan across the feature of interest. A computerized device (not shown) comprising computer software or hardware automates the motion system and data collection, and transforms the raw data into color coordinates. The computerized device guides the user through necessary calibration activities and allows the user to optimize the signal to noise by allowing adjustment of key parameters. Manual adjustment of the sample to selected locations is also possible, if desired.

Figure 2:
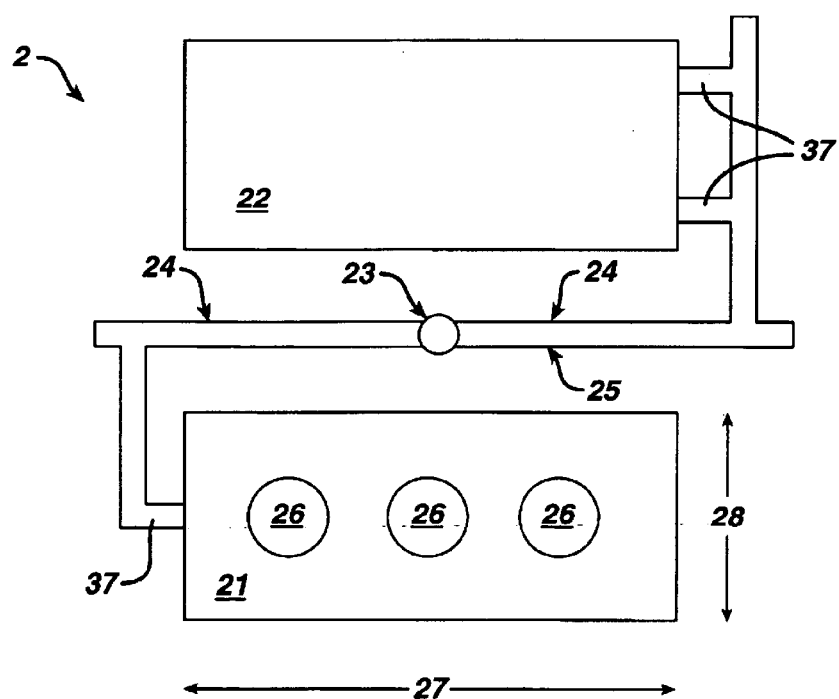
FIG. 2 is a plan view of the molding tool in accordance with one embodiment of the invention.
Figure 3:
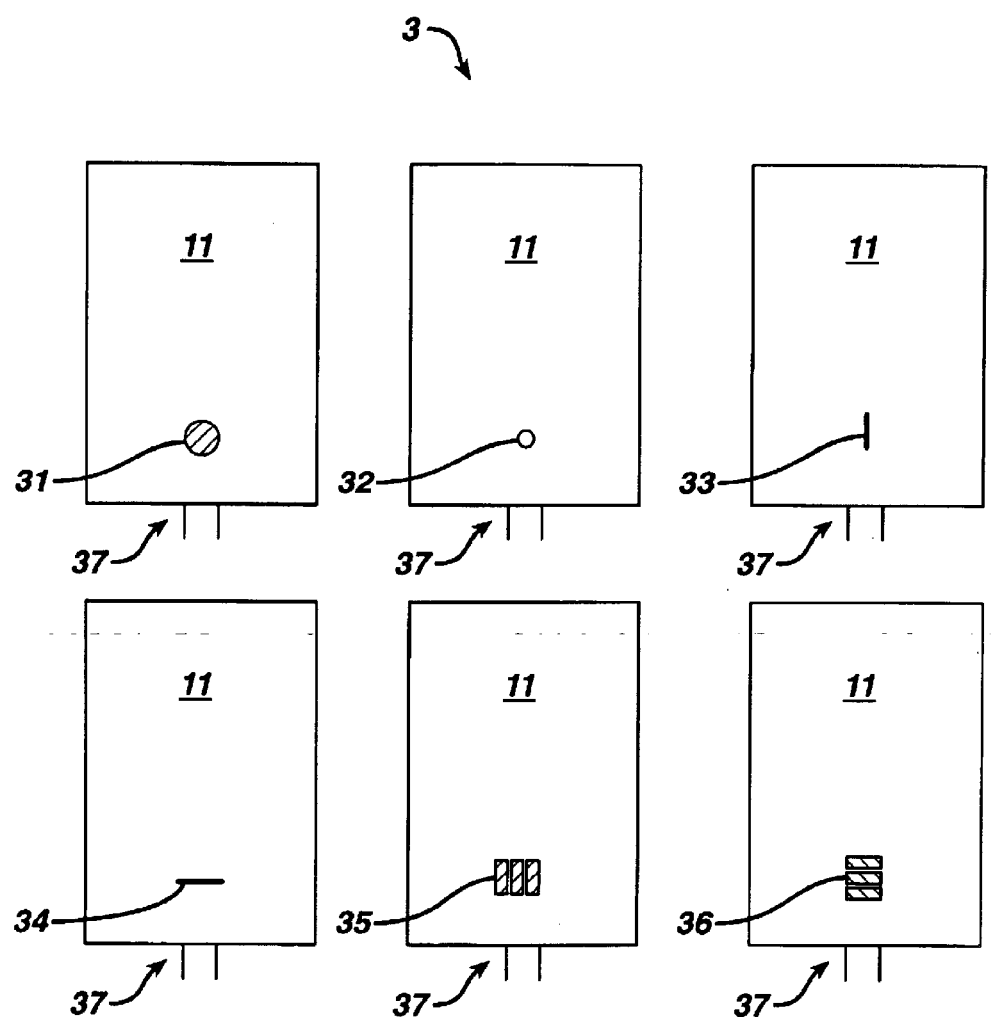
FIG. 3 is a plan view illustrating various mold configurations for use in connection with the molding tool of FIG. 2.

The molding tool, illustrated in FIGS. 2 and 3, comprises a system that allows the user to duplicate streaking from real parts on a laboratory scale. Samples produced in the molding tool are typically flat with a smooth, uniform surface finish, making them the ideal samples to be evaluated using the spatially resolved spectrometer.

A sample mold, such as a two-cavity molding tool 2 illustrated in the preferred embodiment of FIG. 2, comprises a single gate cavity 21 to produce single-gate plaques, and a double-gate cavity 22 used to produce double-gate plaques with knit lines. Extrusion of molten plastic from sprue 23 into one or both cavities 21 and 22 is controlled by valves at appropriate locations 24 in runner 25, and may be shut off or turned on as needed. A variety of inserts may then be placed into one or more insert receptacles to obstruct the flow (increase the chance to have streaking), for example, at any or all of the three different insert locations 26 in the single-gate cavity as shown. Molten plastic enters cavities 21 or 22 through gates 37.

While the dimensions can obviously be varied widely within the scope of the invention, cavity 21 and 22 have a preferred length 27 of approximately four to six inches, and typically about five inches, a preferred width 28 of approximately two to four inches, and typically about three inches, and a preferred thickness (not shown) of approximately 1/32 to 1/8 inch, and typically about 1/16 inch. The goal is to have small-scale, easily molded and handled samples, which have a smooth, flat surface finish for best evaluation using the spectrometer. Thus, any particular size and thickness may be chosen within the scope of the invention which best duplicates the results seen in production samples on a smaller scale, even outside the ranges enumerated above. Thickness, in particular, may depend on plastic formulation, properties such as melt temperature and viscosity, and final production part thickness. Insofar as weight in concerned, a Cycoloy C6200 part and runner, for example, weighs approximately 1.2 oz (33 g). While the Cycoloy C6200 is used for a specific plastic formulation, any formulation of interest could be used for producing sample plastic parts according to the invention. The weights would generally be similar for different plastic formulations.

FIG. 3 illustrates various sample plastic part (plaque) 11 configurations that can be produced utilizing various mold inserts in connection with the molding tool of FIG. 2. In particular, a plurality of molding tool inserts are inserted into one or more of the insert location 26 of molding tool 2. Each such insert is designed to produce, for example, molds (plaques) 11 with a "hole" 31, "boss" 32, "rib" parallel to the plastic flow 33, "rib" across the plastic flow 34, "grill" parallel to the plastic flow 35, and "grill" across the plastic flow 36. The configurations illustrated in FIG. 3 are produced by placing a single "topological" insert into the insert location 26 closest to gate 37 of single gate cavity 21, and a pair of "blank" inserts into the remaining two insert location 26 of single gate cavity 21. Thus, the molding tool inserts are illustrated in terms of the "negative" of the surface features 31, 32, 33, 34, 35, 36 illustrated in FIG. 3. It is understood therefor, that reference to, for example, a "boss" insert 32 refers to an insert that when inserted into single gate cavity 21, and after molten plastic is extruded into single gate cavity 21, will produce the topological surface feature illustrated by 32. Similarly, general references to molding tool inserts 3, will be understood to refer to molding tool inserts that embody the negatives of, and produce surface features such as, those illustrated in connection with the six plaques 11 of FIG. 3.

The six particular configurations illustrated in FIG. 3 are typical of the "topological" surface features commonly encountered in "production" plastic moldings, and so enable "sample" moldings to be produced that have surface features that will be produced in the production moldings for the planned production runs. Of course, these are just examples of the types of configurations that can be produced by the inserts, and it is understood that molding tool inserts 3 that are designed to produce additional surface features not expressly illustrated in FIG. 3 may also be developed and used according to the invention. Also, the ribs and grills (and any other surface features produced by other insert types that are not radially symmetric) can be oriented at any angle relative to the main flow through gate 37. Similarly, while double gate cavity 22 utilizes two gates 37 with substantially parallel input, it is understood that any number of gates can be used, with varying relative orientations to one another, in accordance with the invention.

Thus, in use, if it is known that a "production" plastic part to be manufactured is to have certain topological features, either separately or in combination, "topological" molding tool inserts 3 are placed into one or more of the insert locations 26, and "blank" inserts are placed into any remaining insert locations 26. Then, molten plastic is extruded into single gate cavity 21 or double-gate cavity 22 via gates 37. (Double-gate cavity 22 may be used where it is known that the production plastic part will be produced by double gate injection.) The plastic is allowed to harden, and the resulting plaque(s), with surface features such as 31–36, and with double-gate injection features if pertinent, are removed and placed under spatially-resolved spectrometer 1 as earlier described in connection with FIG. 1 The streaking 18 resulting from the topological feature or features of interest (or from double gate if double-gate cavity 22 is used) is then analyzed by spectrometer 1 as discussed below. It is to be noted that the plaque 11 used as an example in the illustration of FIG. 1 is one with a "grill" parallel to the plastic flow 35.

As detailed below in the discussion of FIGS. 4 through 13, post processing using a computerized device comprising hardware or software in appropriate combination, reduces noise by smoothing the raw color scans and calculates the difference in L values (using CIELab color space) between the lightest and darkest points across a streaked region. That is, if a dark line is observed down the part, it is desirable to look at the "normal" color on either side of the line as well as the variation from one "normal" region to the other across the discoloration. Various embodiments are possible. For single-streak parts, Delta L or area under the curve may be calculated. For parts with multiple streaks, the values for each streak may be averaged or the values for each streak may be reported individually. The user may also choose to view either the raw data or the smoothed data with no further post processing. While this invention is described with reference to CIELab color space, it is understood that any other means of characterizing and analyzing color can also be used in accordance with the invention.

Once a number of molded plastic part samples have been produced and each has been scanned by spatially-resolved spectrometer 1 according to the invention as described in reference to FIGS. 1 through 3, it is desirable to compare the various samples and determine which sample has the optimum appearance. This in turn makes it possible to determine which mix of ingredients and which set of processing conditions should be used in production.

There are three primary types of data that are made available for this purpose according to the invention. First, since the slopes of the peak and valley curves represent how rapidly color variations take place from one space to the next in any given sample, and since smoother (lower slope) variations are preferred to sharper (higher slope) variations, it is desirable to obtain a "quality" measurement based on these slopes. Second, it is desirable to obtain a detailed description of the overall shape characteristics of the appearance of the sample. Finally, one measure of the desirability of any given sample is based on height variation from each peak to the adjacent valley, as well as on an overall average of these. In all cases, since there will be statistically insignificant color variations measured from one linear position to the next for any given sample, it is desirable prior to performing any of these calculations to filter out these insignificant variations to obtain a plotting of true peaks and valleys, over the space being considered, for each sample.

Figure 4:
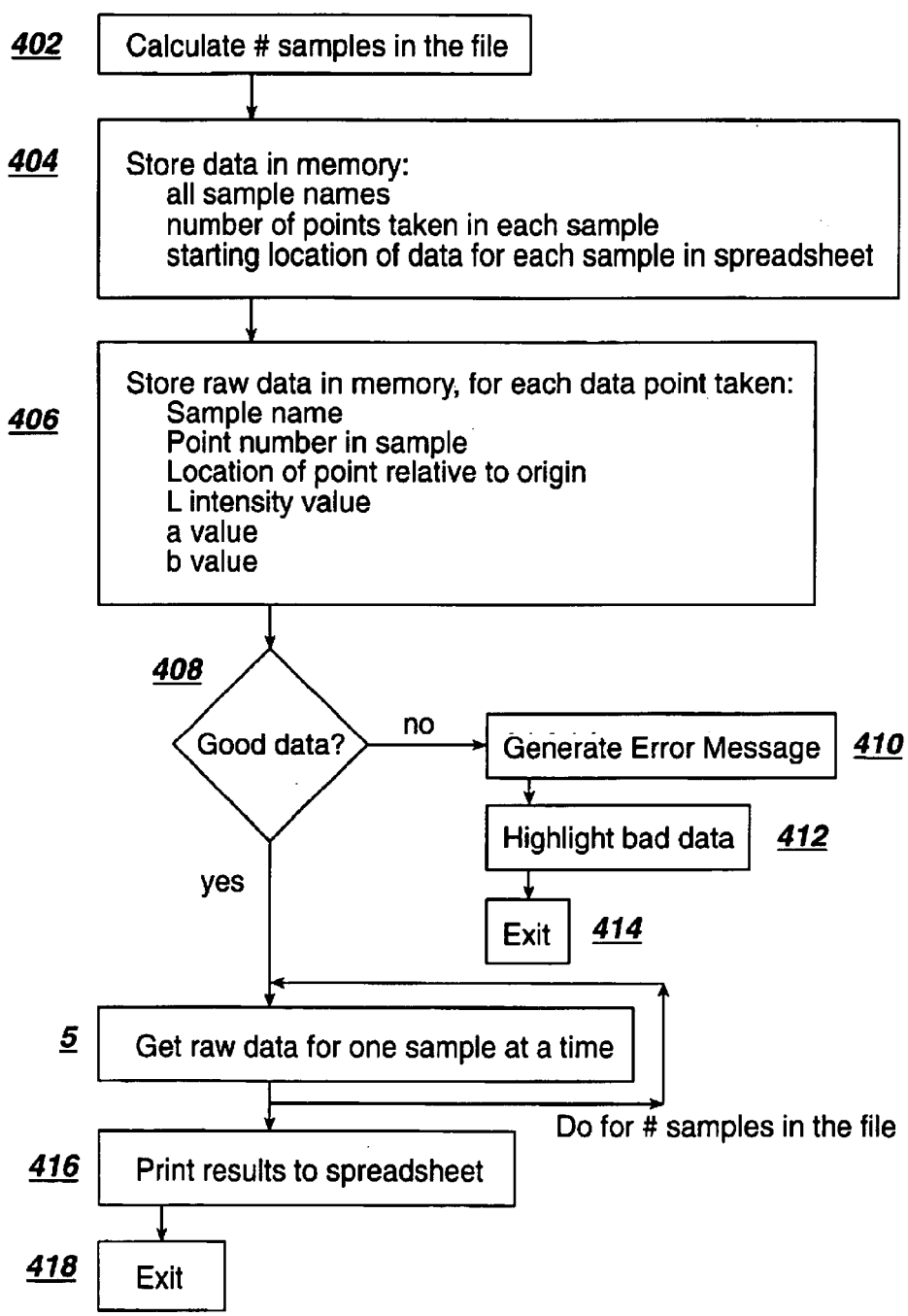
FIGS. 4 and 5 are flowcharts illustrating methods of post-processing color readings according to embodiments of the invention.
Figure 5:
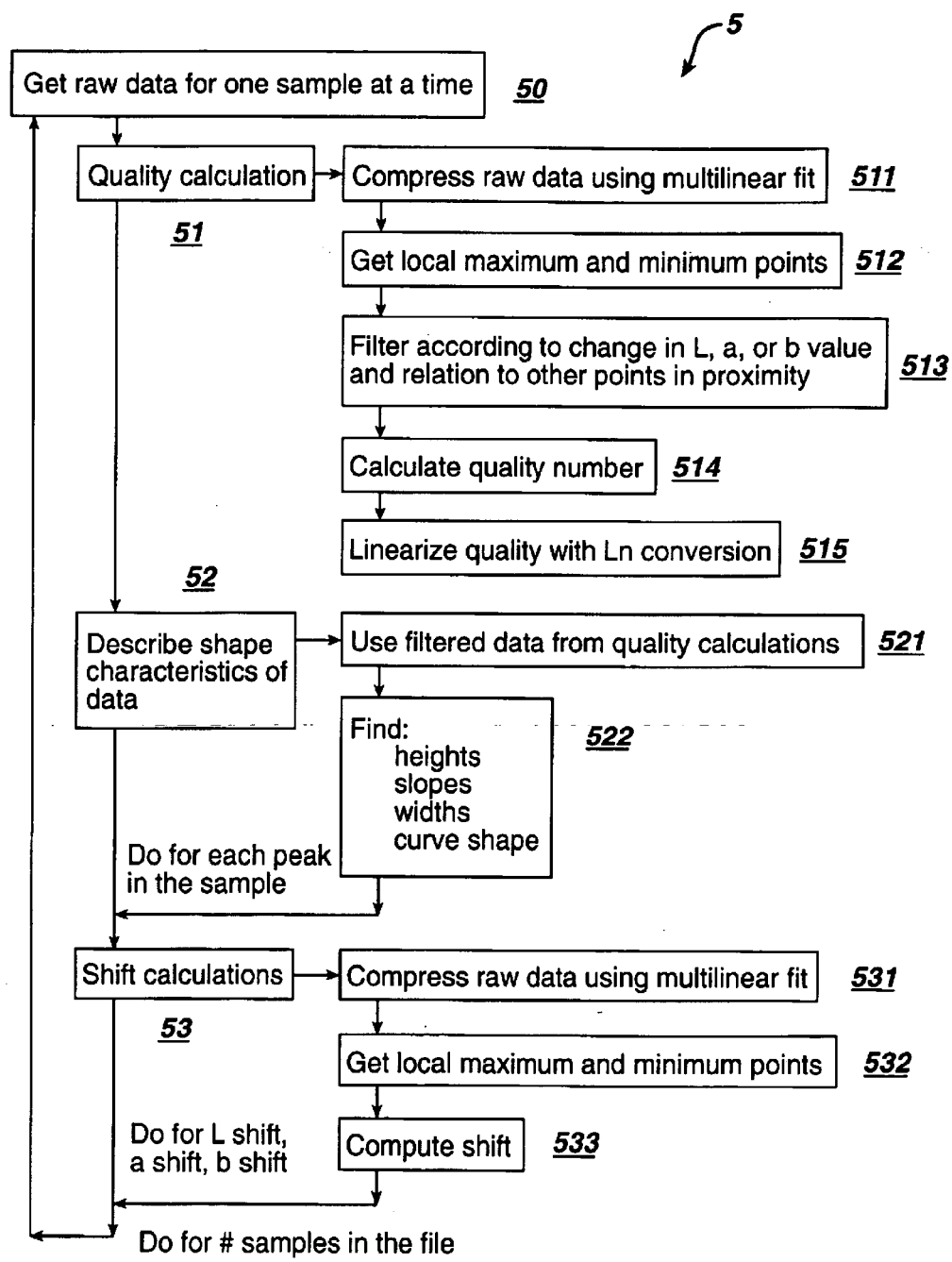

FIGS. 4 and 5 are flowcharts illustrating this overall calculation process. At 402, computerized device 101 first determines the overall number of plastic part samples 11 that have been scanned for analysis. In the discussion to follow, the term "sample" or "sample data" will generally be used to refer to the overall set of CIELab (or similar measure) color data points obtained by the process outlined in FIGS. 1 through 3, for each plastic part sample. For example, if a dozen plastic part samples were produced and scanned, there would be twelve sets of sample data associated with these twelve part samples, and each data sample would contain a number of data points. At 404, names or similar identifiers associated with each sample are established, along with the number of data points for each sample. The first data point for each sample is similarly identified. At 406, each data point is stored in the computerized device with several associated pieces of information, including the sample name or identifier, the number of that particular point in the overall sample, the spatial position of that point relative to the origin (i.e., the first data point for that sample), and the L, a and b values. At 408, the data is examined for completeness. It is determined if all required data fields are present (sample name or identifier, point number in sample, spatial location on sample, L, a, b) and if the numerical fields (all but the name) are numerical. From 408, incomplete raw data is eliminated at 410, 412 and 414, while complete raw data is then analyzed for one sample at a time at 5, using the process summarized below in connection with FIG. 5, until the analysis is complete for all samples. The results are then output at 416 to a suitable data output device such as a spreadsheet, computer display monitor, printer, etc. in a suitable data format such as numeric data, graphical representation, etc. The process concludes at 418.

Figure 6:
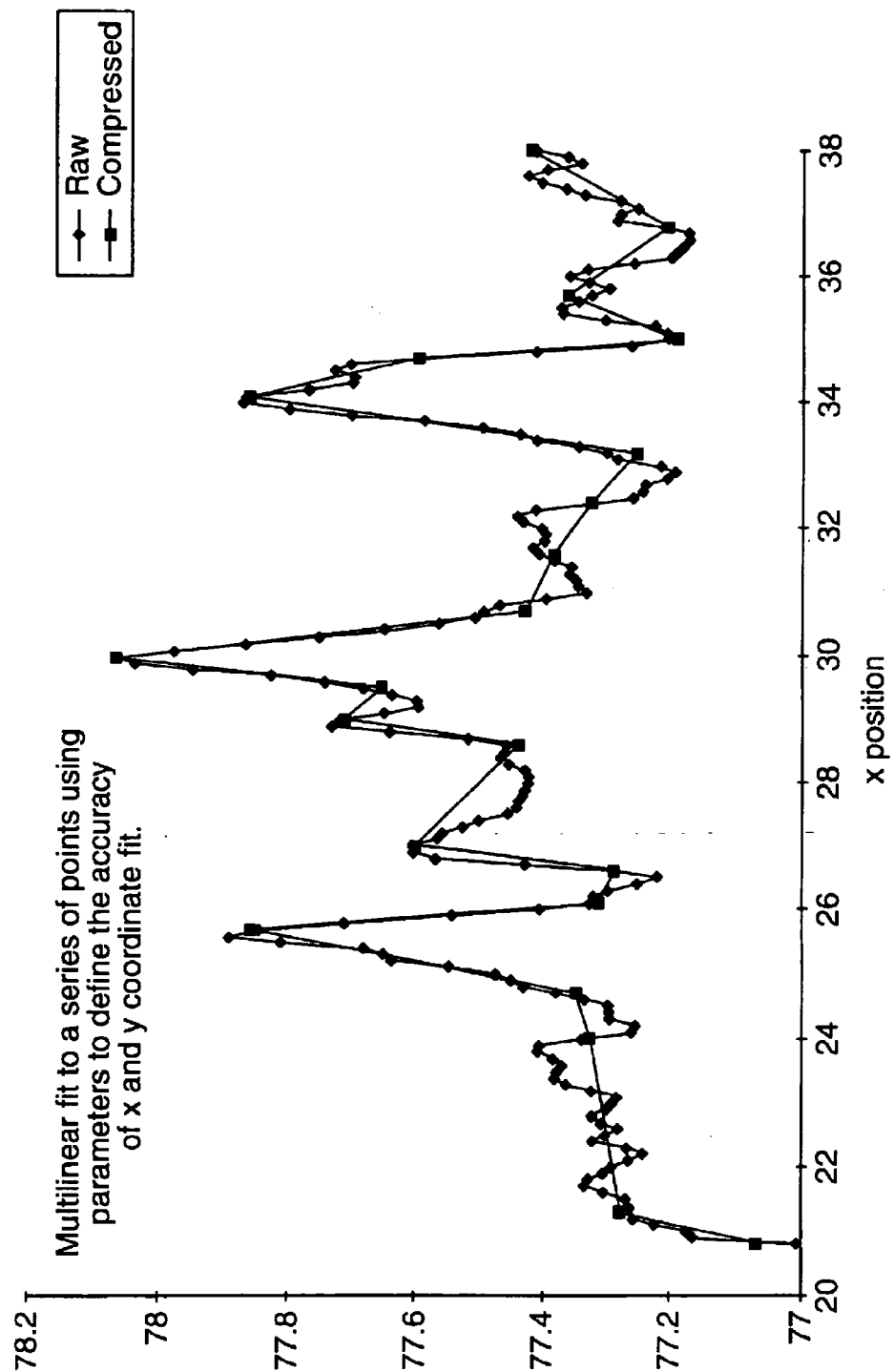
FIGS. 6 through 9 illustrate sample data representative of color signal shape including peaks and valleys, as that data undergoes several iterations of post processing filtering according to the invention.
Figure 7:
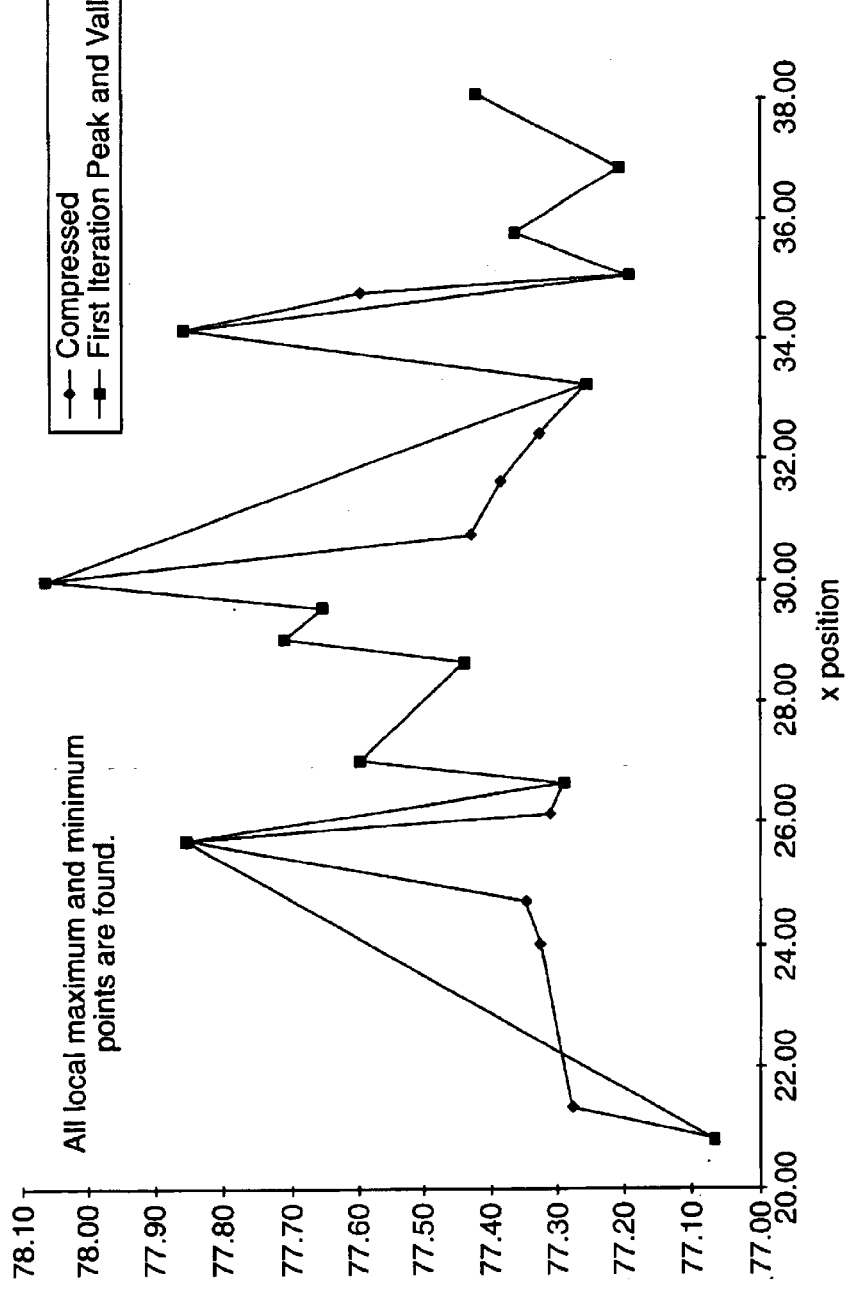
Figure 8:
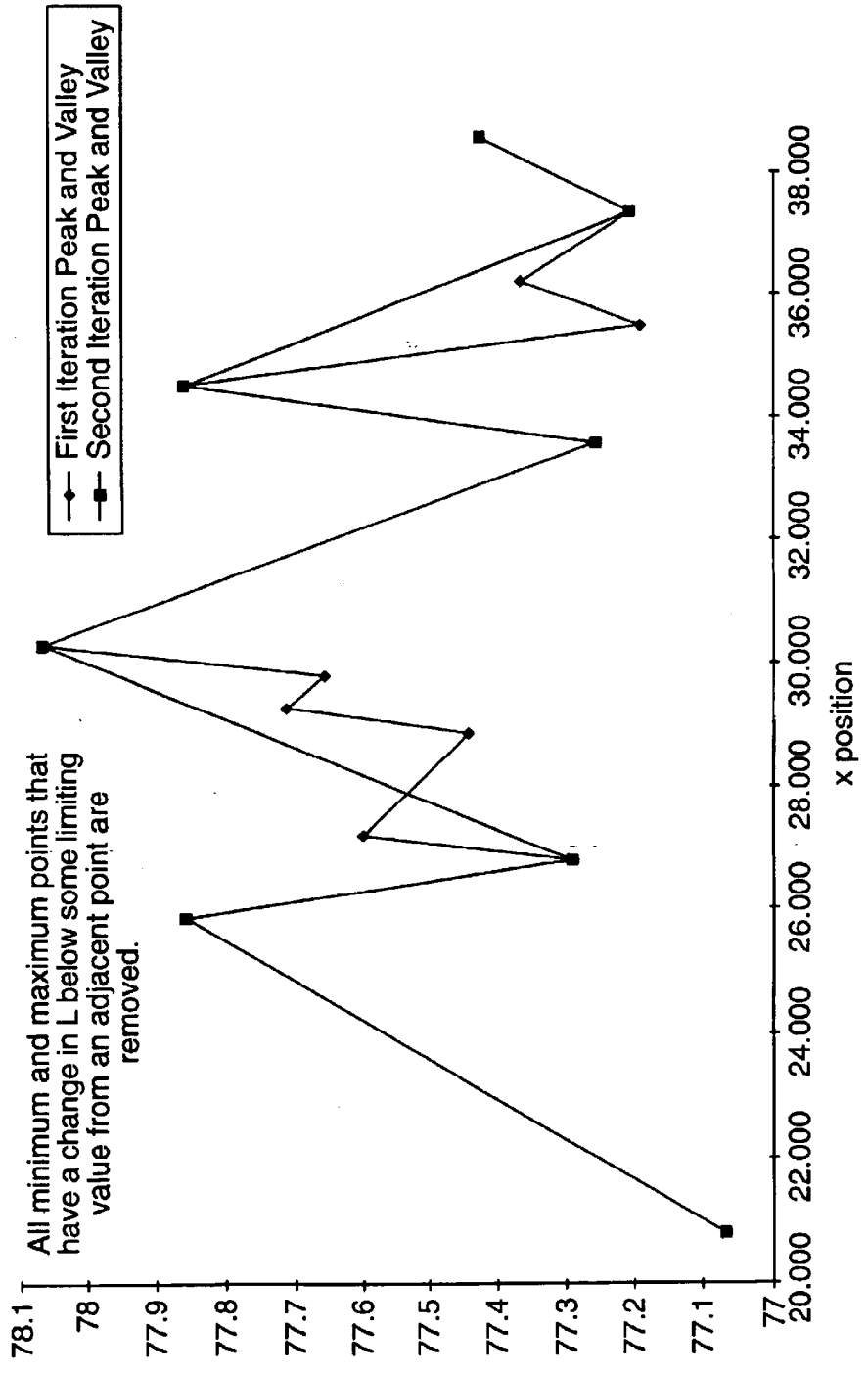
Figure 9:
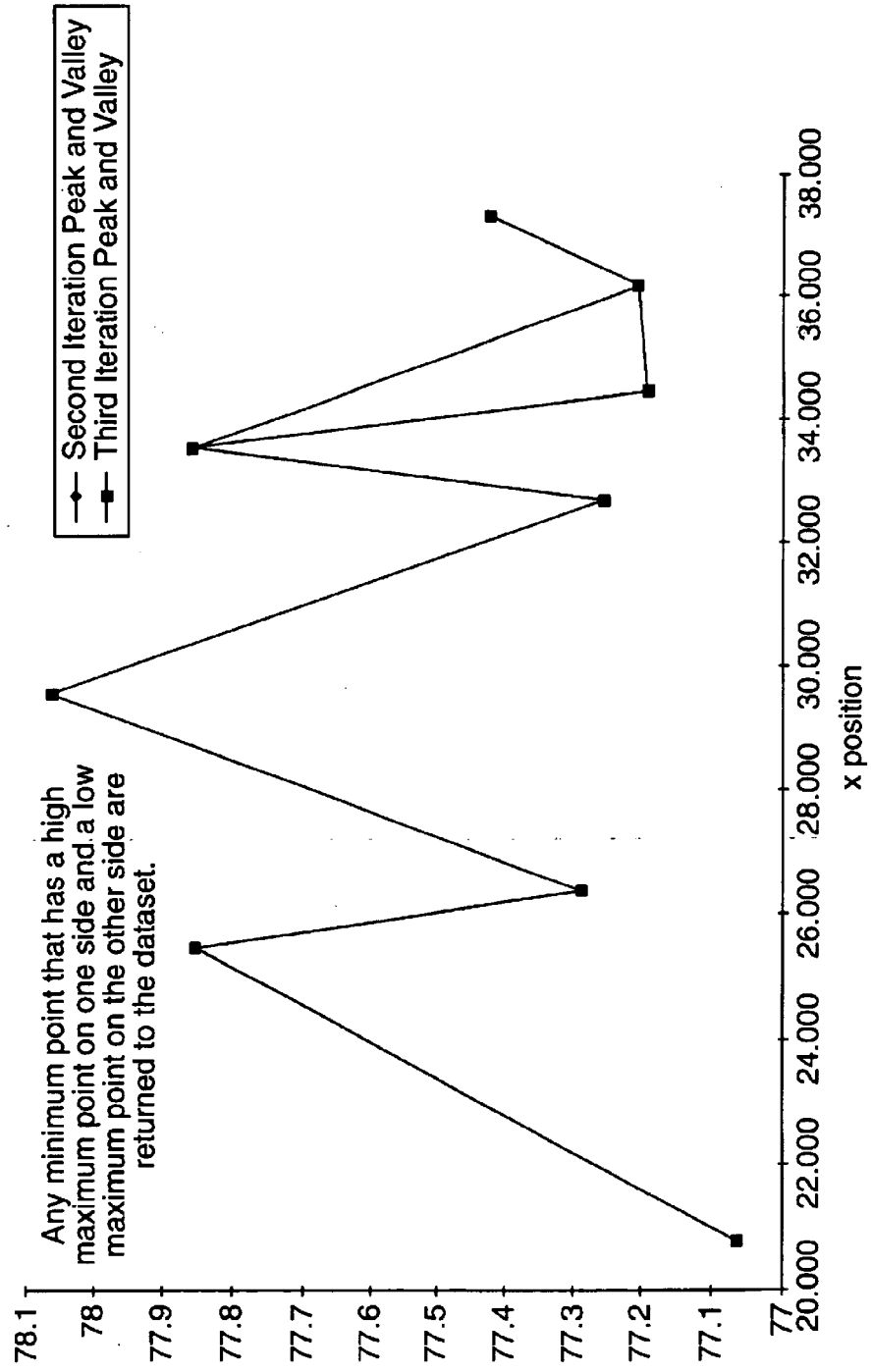

In FIG. 5, which comprises step 5 of FIG. 4 and illustrates the overall processing of data for a single sample, computerized device 101 first obtains the raw data for the given sample at 50. Then the first of the three above-referenced calculations—the quality calculation 51—begins;

At 511, small fluctuations in L, a, b indiscernible to the human eye are filtered out, using a multilinear fit to a series of points using parameters to define the accuracy of the x and y coordinate fit. As illustrated in FIG. 6, local "noise" in the raw data is filtered out, and only variations above certain predefined threshold parameters are maintained. This results in the "compressed" data plot superimposed over the corresponding "raw" data plot in FIG. 6. At 512 and 513, this compressed data is then further filtered through several iterations (in this example, three) illustrated in FIGS. 7, 8 and 9. The first iteration at 512 (FIG. 7) identifies all local extreme, i.e., maximum and minimum, points. Detecting local minimum and maximum values allows determination of defects or inconsistencies in the sample such as "streaking." The second iteration at 513 (FIG. 8) removes from the data set, all minima and maxima with a change in L (or a and b for those calculations) from the adjacent minima and maxima below a predetermined limiting value, so that only significant variations are maintained. The third and final iteration, also at 513 (FIG. 9) then returns to the data set any minimum point that has a high maximum point on one side and a low maximum point on the other side. The data output from 513, illustrated by the example in FIG. 9, will be henceforth referred to as (final iteration) "filtered" data. Fluctuations in L, a and b vales following this filtering indicate changes in the appearance of the sample.

Figure 10:
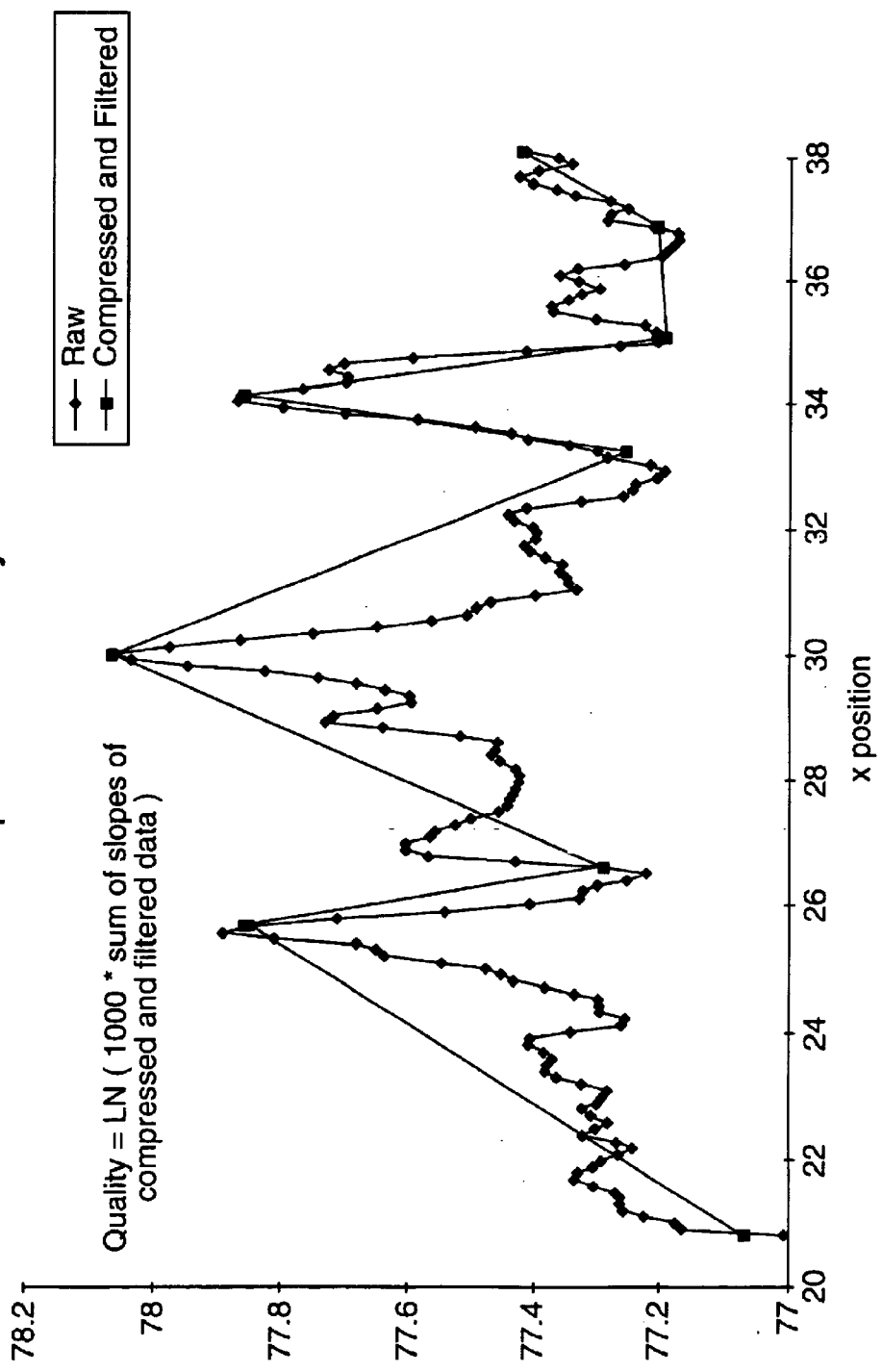
FIG. 10 illustrates a method used to calculate a quality measure of the sample under consideration according to one embodiment of the invention, from the sample data of FIGS. 6–9.

Next, a quality number is calculated at 514. The Quality number is a way of ranking the samples according to the number of streaks apparent and the signal intensity shift. It is linearized 515 so that ranking of several test samples is scaled correctly. FIG. 10 illustrates a sample calculation of this quality number. If Q=quality number, $\Sigma\ dL/dx$=the sum of the slopes of the filtered data from 513, and M=a suitable multiplier such as 1000, then:

$$Q=\ln(M*\Sigma\ DL/dx) \quad (1)$$

Similarly, for a and b data, once simply substitutes a and b for L in the above. By its relation to the first derivative (slope) of the L, a and b curves, Q essentially measures the smoothness or sharpness of any measured streaking. As noted above, this is the first of the three primary measures used to determine which among all samples is to be used as the basis for a full-scale production recipe.

Figure 11:
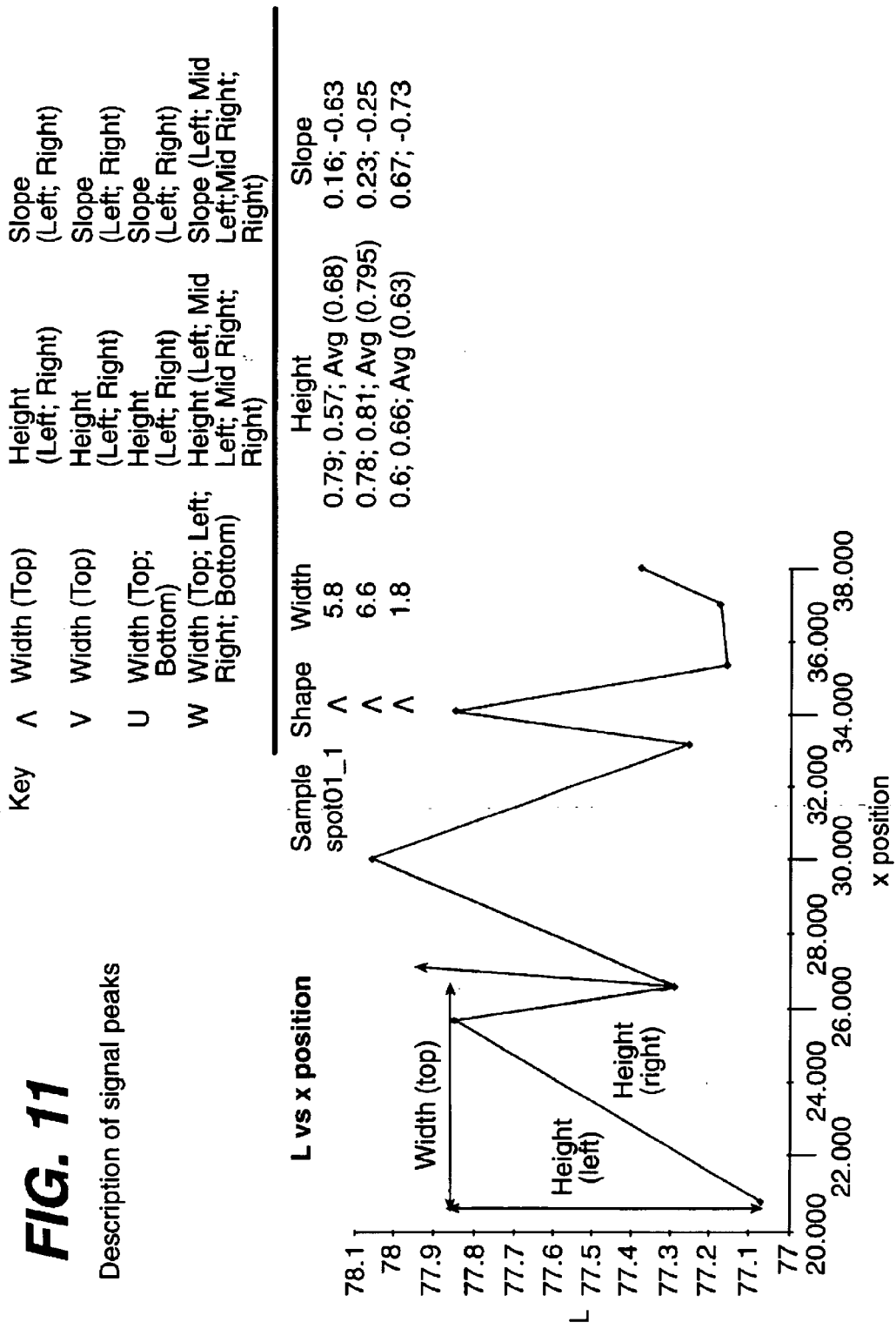
FIG. 11 illustrates the method used to describe the shape of the sample data of FIGS. 6–9.

Next, at 52, the overall shape characteristics of the data are described, using the same filtered data from 513 (illustrated in FIG. 9) that was used to calculate quality number 0. Using this filtered data at 521, one arrives at a clear representation of signal peaks that can then be quantified in various ways as shown in FIG. 11. Data taken from various samples in fact shows that different types of defects give different looking peak shapes. At 522, descriptive data such as height, slope, width, and curve shape allows the user to quantify and qualitatively describe the difference between samples. The number of defects in a sample as well as the signal intensity of each individual defect are important to the user. This is the second of the three primary measures used to determine which among all samples is to be used as the basis for a full-scale production recipe. Some example width, height and slope data resulting from shape analysis 52 are illustrated toward the upper right of FIG. 11.

Finally, L, a, and b shift calculations are performed at 53 to describe the signal intensity shift and color shift across the sample taken. Whereas quality calculation 51 and shape analysis 52 share the same compressed 511 and filtered 513, 521 data, shift calculation 53 in the preferred embodiment does not. At 531, local "noise" in the raw data is filtered out, and only variations above certain predefined threshold parameters are maintained, resulting in a second compressed data set similar to that obtained in 511. However, it is generally preferred to use a different set of threshold parameters for shift calculations 53 than for quality 51 and shape 52 calculations and analysis. Similarly to 512, local maximum and minimum points are again obtained 532, but again, these are based on the preferably different threshold parameters used at 531. The three filtering iterations 513 are not performed. Then, at 533, the shift is computed. FIG. 13 illustrates this for a sample L shift calculation. Peaks below a certain predetermined threshold height are then discarded, and the L shift, as well as a and b shifts, are calculated from peaks above that predetermined threshold 512. If S=shift, T=total sum of peak heights above threshold, and N=number of peak heights above threshold, then $$S=T/N. \quad (2)$$

That is, the shift simply measures the average peak height of a given sample, which as noted earlier, is the third of the three primary measures used to determine which among all samples is to be used as the basis for a full-scale production recipe. If desired, the individual shifts may be reported rather than the average.

It is understood that FIGS. 6 through 13 illustrate graphical representations of numeric data stored in and operated upon by computerized device 101, and of course, that FIGS. 6 thorough 13 are simply illustrative of the invention and not limiting. It is further understood that this numeric data, including numeric data indicative of such features as coordinates, slopes, shapes, etc., can be represented within computerized device 101 in a wide variety of ways that would be apparent to someone of ordinary skill. Finally, it is understood that specific manners of representing the numeric data underlying FIGS. 6 through 13 in computerized device 101 using practices common in the art is considered to be within the scope of the invention and the claims associated therewith.

This system may be used to quantify all manner of appearance defects, including light and dark streaks, splay, surface defects (gloss or roughness), and others.

While only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

What is claimed is:

1. A system to identify and quantify appearance defects in molded plastic parts, comprising:
   a molding tool having pre-determined topological features for simulating sing phenomenon, for producing sample plastic parts;
   a spatially-resolved spectrometer for obtaining a plurality of raw data readings of reflected light from sample points of at least one of said sample plastic parts; and
   a computerized device for post-processing said raw data readings by analyzing, filtering and quantifying said readings, said computerized device generating a quality number Q indicative of at least one of a number and intensity of streaks in said sample plastic parts.

2. The system of claim 1, wherein said molding tool further comprises:
   a cavity comprising at least one gate, wherein
   molten plastic is extruded through said at least one gate into said cavity to produce said sample plastic parts with any appearance defects resulting from said extrusion through said at least one gate.

3. The system of claim 1, wherein said molding tool further comprises:
   a cavity comprising at least one gate and at least one insert location; and
   at least one molding tool insert with at least one negative topological feature thereof, inserted into said at least one insert location; wherein
   molten plastic is extruded through said gate into said cavity to produce said sample plastic parts with positive topological surface features corresponding to said negative topological features of said at least one molding tool insert, and with any appearance defects resulting from said positive topological surface features.

4. The system of claim 3, wherein said negative and corresponding positive topological features are selected from the topological feature group consisting of:
   a flat, null surface;
   a hole;

a boss;
a rib at an angle between zero and 45 degrees relative to said extrusion of said molten plastic through said gate;
a rib at an angle between 45 and 90 degrees relative to said extrusion of said molten plastic through said gate;
a grill at an angle between zero and 45 degrees relative to said extrusion of said molten plastic through said gate; and
a grill at an angle between 45 and 90 degrees relative to said extrusion of said molten plastic through said gate.

5. The system of claim 1, wherein said computerized device further comprises:
computerized data compression means for calculating compressed data by filtering out local noise below a predetermined threshold, from said raw data;
computerized first iteration filtering means for calculating first iteration filtered data by identifying local extreme points comprising maximum and minimum points in said compressed data;
computerized second iteration filtering means for calculating second iteration filtered data by removing from said first iteration filtered data, any of said local extreme points that vary with respect to an adjacent local extreme point by a magnitude below a predetermined limiting value; and
computerized third iteration filtering means for calculating a final iteration filtered data graph by returning to said second iteration filtered data, any minimum point that has an adjacent high maximum point on one side thereof and an adjacent low maximum point on an other side thereof.

6. The system of claim 5, wherein said computerized device further comprises:
computerized quality calculation means for calculating and linearizing from said final iteration filtered data graph, said quality number Q given by:

$$Q=\ln (M^* \Sigma \ dL/dx),$$

where $\Sigma \ dL/dx$ represents a sum of slopes of said final iteration filtered data and M is a linearization multiplier.

7. The system of claim 5, wherein said computerized device further comprises:
computerized shape calculation means for deriving from said final iteration filtered data graph, at least one data shape descriptor selected from the data shape descriptor group consisting of:
a height of at least one of said maximum points with respect to at least one minimum point adjacent thereto;
a slope of said filtered data graph between at least one of said maximum points and at least one minimum point adjacent thereto;
a width of said filtered data graph between at least one pair of selected local extreme points; and
a curve shape of at least one region of said filtered data graph.

8. The system of claim 1, wherein said computerized device further comprises:
computerized data compression means for calculating compressed data by filtering out local noise below a predetermined noise threshold, from said raw data, and by identifying local extreme points comprising maximum and minimum points in said raw data; and
computerized shift calculation means for calculating an average peak height of said local extreme points of said compressed data, wherein the average shift S in said peak-heights is calculated as:

$$S=T/N,$$

where T represents a total sum of peak heights above a predetermined height threshold, and N represents a number of said peak heights above said predetermined height threshold.

9. A method to identify and quantify appearance defects in molded plastic parts, comprising the steps of:
producing sample plastic parts using a molding tool, said molding tool having predetermined topological features for simulating streaking phenomenon;
obtaining a plurality of raw data readings of reflected light from sample points of at least one of said sample plastic parts using a spatially-resolved spectrometer; and
analyzing, filtering and quantifying said readings by post-processing said raw data readings using a computerized device to generate a quality number Q indicative of at least one of a number and intensity of streaks in said sample plastic parts.

10. The method of claim 9, said step of producing said sample plastic parts using said molding tool further comprising the step of:
extruding molten plastic through at least one gate into a cavity thereby so-producing said sample plastic parts with any appearance defects resulting from said extrusion through said at least one gate.

11. The method of claim 9, said step of producing said sample plastic parts using said molding tool further comprising the steps of:
inserting at least one molding tool insert with at least one negative topological feature thereof, into at least one insert location of a cavity; extruding molten plastic through at least one gate into said cavity thereby so-producing said sample plastic parts with positive topological surface features corresponding to said negative topological features of said at least one molding tool insert, and with any appearance defects resulting from said positive topological surface features.

12. The system of claim 11, comprising the further step of selecting said negative and corresponding positive topological features from the topological feature group consisting of:
a flat, null surface;
a hole;
a boss;
a rib at an angle between zero and 45 degrees relative to said extrusion of said molten plastic through said gate;
a rib at an angle between 45 and 90 degrees relative to said extrusion of said molten plastic through said gate;
a grill at an angle between zero and 45 degrees relative to said extrusion of said molten plastic through said gate; and
a grill at an angle between 45 and 90 degrees relative to said extrusion of said molten plastic through said gate.

13. The method of claim 9, said step of analyzing ad quantifying said readings by post-processing said raw data readings using said computerized device comprising the further steps of:
calculating compressed data from said raw data by filtering out local noise below a predetermined threshold;
calculating first iteration filtered data by identifying local extreme points comprising maximum and minimum points in said compressed data;

calculating second iteration filtered data by removing from said first iteration filtered data, any of said local extreme points that vary with respect to an adjacent local extreme point by a magnitude below a predetermined limiting value; and calculating a final iteration filtered data graph by returning to said second iteration filtered data, any minimum point that has an adjacent high maximum point on one side thereof and an adjacent low maximum point on an other side thereof.

14. The method of claim 13, comprising the further step of:

calculating and linearizing from said final iteration filtered data graph, said quality number Q given by:

$$Q=\ln(M^* \Sigma\ dL/dx),$$

where $\Sigma\ dL/dx$ represents a sum of slopes of said final iteration filtered data and M is a linearization multiplier.

15. The method of claim 13, comprising the further steps of:

deriving from said final iteration filtered data graph, at least one data shape descriptor selected from the data shape descriptor group consisting of:

a height of at least one of said maximum points with respect to at least one minimum point adjacent thereto;

a slope of said filtered data graph between at least one of said maximum points and at least one minimum point adjacent thereto;

a width of said filtered data graph between at least one pair of selected local extreme points; and a curve shape of at least one region of said filtered data graph.

16. The method of claim 9, said step of analyzing and quantifying said readings by post-processing said raw data readings using said computerized device comprising the further steps of:

calculating compressed data by filtering out local noise below a predetermined noise threshold, from said raw data, and by identifying local extreme points comprising maximum and minimum points in said raw data; and calculating an average peak height of said local extreme points of said compressed data, wherein the average shift S in said peak heights is calculated as:

$$S=T/N,$$

where T represents a total sum of peak heights above a predetermined height threshold, and N represents a number of said peak heights above said predetermined height threshold.

17. A system to identify and quantify appearance defects in molded plastic parts comprising:

a molding tool for producing sample plastic parts;

a spatially-resolved spectrometer for obtaining a plurality of raw data readings of reflected light from sample points of at least one of said sample plastic parts; and a computerized device for post-processing said raw data readings by analyzing, filtering and quantifying said readings wherein said computerized device further comprises:

computerized data compression means for calculating compressed data by filtering out local noise below a predetermined threshold, from said raw data;

computerized first iteration filtering means for calculating first iteration filtered data by identifying local extreme points comprising maximum and minimum points in said compressed data;

computerized second iteration filtering means for calculating second iteration filtered data by removing from said first iteration filtered data, any of said local extreme points that vary with respect to an adjacent local extreme point by a magnitude below a predetermined limiting value;

computerized third iteration filtering means for calculating a final iteration filtered data graph by returning to said second iteration filtered data, any minimum point that has an adjacent high maximum point on one side thereof and an adjacent low maximum point on an other side thereof; and computerized quality calculation means for calculating and linearizing from said final iteration filtered data graph, a quality number Q given by:

$$Q=\ln(M^* \Sigma\ DL/dx),$$

Where $\Sigma\ dL/dx$ represents a sum of slopes of said final iteration filtered data and M is a linearization multiplier.

18. A method to identify and quantify appearance defects in molded plastic parts, comprising the steps of:

producing sample plastic parts using a molding tool;

obtaining a plurality of raw data readings of reflected light from sample points of at least one of said sample plastic parts using a spatially-resolved spectrometer; and analyzing, filtering and quantifying said readings by post-processing said raw data readings using a computerized device wherein said step of analyzing filtering and quantifying said readings by post-processing said raw data readings using said computerized device comprising the further steps of:

calculating compressed data from said raw data by filtering out local noise below a predetermined threshold;

calculating first iteration filtered data by identifying local extreme points comprising maximum and minimum points in said compressed data;

calculating second iteration filtered data by removing from said first iteration filtered data, any of said local extreme points that vary with respect to an adjacent local extreme point by a magnitude below a predetermined limiting value;

calculating a final iteration filtered data graph by returning to said second iteration filtered data, any minimum point that has an adjacent high maximum point on one side thereof and an adjacent low maximum point on an other side thereof; and calculating and linearizing from said final iteration filtered data graph, a quality number Q given by:

$$Q=\ln(M^* \Sigma\ dL/dx),$$

where $\Sigma\ dL/dx$ represents a sum of slopes of said final iteration filtered data and M is a linearization multiplier.

* * * * *

UNITED STATES PATENT AND TRADEMARK OFFICE
CERTIFICATE OF CORRECTION

PATENT NO. : 6,868,371 B1
DATED : March 15, 2005
INVENTOR(S) : Feldman et al.

It is certified that error appears in the above-identified patent and that said Letters Patent is hereby corrected as shown below:

Column 1,
Line 60, after "parts" delete "," and insert therefor -- . --

Column 7,
Line 6, after "b" delete "vales" and insert therefor -- values --
Line 29, after "number" delete "O." and insert therefor -- Q. --

Column 8,
Line 33, after "simulating" delete "sing" and insert therefor -- streaking --

Column 10,
Line 58, after "analyzing" delete "ad" and insert therefor -- and --

Signed and Sealed this

Ninth Day of August, 2005

JON W. DUDAS
*Director of the United States Patent and Trademark Office*